US006375976B1

(12) United States Patent
Roden et al.

(10) Patent No.: US 6,375,976 B1
(45) Date of Patent: Apr. 23, 2002

(54) MULTI-PURPOSE ACID COMPOSITIONS

(75) Inventors: Ernest G. Roden, Hodge; John R. Dankert, Lafayette, both of LA (US)

(73) Assignee: SteriFx, Inc., Shreveport, LA (US)

( * ) Notice: Subject to any disclaimer, the term of this patent is extended or adjusted under 35 U.S.C. 154(b) by 0 days.

(21) Appl. No.: 09/487,174

(22) Filed: Jan. 19, 2000

Related U.S. Application Data

(60) Provisional application No. 60/116,628, filed on Jan. 19, 1999.

(51) Int. Cl.$^7$ .......................... A61K 47/00; A61K 7/00; A61K 7/32; A01N 25/34; A61F 9/02
(52) U.S. Cl. .......................... 424/439; 424/65; 424/401; 424/404; 424/436
(58) Field of Search ................ 424/439, 436, 424/404, 401, 65, 443, 402, 405

(56) References Cited

U.S. PATENT DOCUMENTS

| | | | |
|---|---|---|---|
| 4,181,622 A | | 1/1980 | Gavin .................. 252/143 |
| 4,199,469 A | | 4/1980 | Walzer ................. 252/146 |
| 4,250,048 A | | 2/1981 | Leveskis ............... 252/142 |
| 4,459,202 A | | 7/1984 | Garcia ................. 208/11 LE |
| 4,477,364 A | | 10/1984 | Garcia ................. 252/142 |
| 4,483,887 A | | 11/1984 | Garcia ................. 427/436 |
| 4,675,120 A | | 6/1987 | Martucci .............. 252/8.553 |
| 4,762,726 A | * | 8/1988 | Soucie et al. .......... 426/602 |
| 4,970,014 A | | 11/1990 | Garcia ................. 252/79.3 |
| 4,970,015 A | | 11/1990 | Garcia ................. 252/79.4 |
| 5,019,288 A | | 5/1991 | Garcia ................. 252/79.2 |
| 5,512,200 A | * | 4/1996 | Garcia ................. 252/142 |

OTHER PUBLICATIONS

"Decontamination", pp. 127–359, Medical Management of Chemical Casualties Handbook, 2nd Ed., Medical Research Institute of Chemical Defense, Sep. 1995.
"Sterilants and High Level Disinfectants cleared by FDA in a 510(k) as of Oct. 1, 1998 with General Claims for Processing Reusable Medical and Dental Devices", Center for Devices and Radiological Health, U.S. Food and Drug Administration (Jan. 1999).
Cohen, P. T. et al., Chapter 10.4, Table 1, "Chemical agents for disinfection and sterilization," The AIDS Knowledge Base, 1994 (http://hivinsite.ucsf.edu/akb/1994/index.html).
Avia Technologies, Inc. Brochure, "Chem Shield", 1989.
Hurst, C.G., "Decontamination", Medical Aspects of Chemical and Biological Warfare, Textbook of Military Medicine, Part I, Warfare, Weaponry and the Casualty, Chap. 15, pp. 351–359 (1996).

\* cited by examiner

*Primary Examiner*—Thurman K. Page
*Assistant Examiner*—S. Tran
(74) *Attorney, Agent, or Firm*—Heller Ehrman White & McAuliffe LLP

(57) ABSTRACT

The invention relates to solutions containing acidic compositions that have a pH of less than 1, are non-caustic to human tissue and are safe for human ingestion. These compositions may be used as the sole or major component of solutions such as cleansers, pharmaceuticals, food preservatives and disinfectants. The acidic compositions may be used in medical, industrial, military and household applications. The invention also relates methods of administering and using the acidic compositions of the invention.

24 Claims, No Drawings

MULTI-PURPOSE ACID COMPOSITIONS

REFERENCE TO RELATED APPLICATIONS

The application claims priority to U.S. provisional patent application, entitled "Multi-Purpose Acid Compositions," serial No. 60/116,628, filed Jan. 19, 1999.

BACKGROUND

1. Field of the Invention

The present invention relates to acid compositions that are useful in food, medical, commercial and military industries and also as general household products. These compositions have a low pH, are relatively non-corrosive to metals, do not harm skin and are safe for use in food and beverages. The invention also relates to formulations that contain these acid compositions and to methods for using such formulations.

2. Description of the Background

Low pH compositions and solutions containing acidic compositions are used for various industrial and general household purposes, such as cleaning and sterilizing surfaces and articles of manufacture. Examples include well-known household cleansers and disinfectants, industrial microchip production and cleaning agents, and anti-microbials. To work both effectively and efficiently, these solutions typically contain strong acids or organic solvents, which present health concerns to the user, may be corrosive to the substances they are designed to clean (e.g. metals) and pose an ecological hazard with respect to disposal.

There have been a number of efforts aimed at developing less corrosive and less toxic acidic products. For example, U.S. Pat. No. 4,459,202 is directed to an acidic composition for recovering bituminous products from tar sands. Two strong and two weak acids are combined to form an acidic solvent that can be used to remove and recover the bituminous products. The composition is described as being non-corrosive and less hazardous to handle than other strongly acidic solutions.

The molecular effect of combining first and second strong acids with the third and fourth weaker acids forces the weaker acids to act as conjugate bases for the strong acids and to accept hydrogen ions (actually hydronium ions in aqueous solution) from the strong acids. The resulting acidic solution has a very low pH value, and a large amount of free hydrogen ions. However, the ability of this strong acidic composition to effectively function as a solvent may sometimes require more acid than would be considered safe or non-hazardous to human tissue. Moreover, there is no suggestion that this composition can be used in other applications, such as in products which come into contact with food. In fact, the composition cannot be used in connection with food and drink, as one or more of its components are not listed on the U.S. Food and Drug Administration list of substances considered generally recognized as safe (GRAS).

Various formulations using multiple acid compositions are disclosed in U.S. Pat. Nos. 4,675,120, 4,970,014, 4,970,015 and 5,019,288. Each of these compositions is described as either useful for well-acidizing, tertiary oil recovery, removing rust from metal, cleaning aluminum, radiator cleaning, boiler and heat exchanger cleaning, or copper cleaning. These compositions are described as generally non-corrosive to metal and relatively inert when contacted with human tissue. In addition, U.S. Pat. No. 4,483,887 describes a multiple acid solution useful for metal plating. U.S. Pat. No. 4,477,364 describes a multiple acid solution useful for cleaning glassware.

Although these acid-based solutions may be effective for the various described purposes, a major drawback is that certain formulations can cause skin irritation. For example, studies conducted using a topical skin disinfectant containing the core composition of U.S. Pat. No. 4,459,202 found that the product caused reddening of the skin and a burning sensation. Similar reddening of the skin and burning sensation resulted with a cleaning solution containing the core acid composition of U.S. Pat. No. 4,459,202. As such, these acid compositions cannot be safely used in products where skin contact is a possibility. In addition, such compositions cannot be used in products associated with foods or beverages. Further, many of these compositions require a multiplicity of components, leading to increased production costs.

U.S. Pat. No. 5,512,200 is directed to a multiple acid composition described as non-irritating to the skin and useful as a component of products such as cleansers, cosmetics and pharmaceutical agents. However, at least one of the components is not considered GRAS. Thus, despite the relatively inert nature of this composition, it cannot be used in foods or drinks, or in products associated with foods or drinks.

There is therefore a need for acid compositions comprising a minimum number of component acids, all of which components are approved by the Food and Drug Administration as GRAS, with broad utility for cleaning, sterilizing and anti-microbial uses that are effective, non-toxic and safe for use with food and food-related products.

SUMMARY OF THE INVENTION

The invention overcomes the problems and disadvantages associated with current strategies and designs and provides novel low pH compositions useful in medical, military, industrial and household settings. These acid compositions can be used as the sole or core component of solutions including cleansers, anti-microbial agents, disinfectants, decontaminants, pharmaceuticals, cosmetics, anti-odor agents and sterilants.

The low pH compositions of the present invention are safe for use as either the sole or major component of solutions including, but not limited to, disinfectants, cleansers, sterilizers, cosmetics, and pharmaceutical agents, and can be used in industrial, medical, military and general household settings. The compositions of the present invention are safe not only for use in products which contact human skin, but also for use in ingestible products.

One embodiment of the invention is directed to an acid solution for inhibiting microbial growth comprising an aqueous acidic core composition which makes up 50% to 100% of the solution. The acidic core composition consists of acids that are safe for use in food and drink products and food- and drink-associated products (i.e. GRAS substances). The acidic core composition may be prepared by admixing from about zero to about 25%, by volume, of a first acid, preferably between about 0.1% to about 15%, and more preferably between about 0.5% and about 10%, with between about 1% and about 25%, by volume, preferably between about 2% and about 15%, and more prferably between about 5% and about 10%, of a second acid to produce a first acidic composition.

The first acid is an inorganic acid that dissociates nearly to completion in water. The second acid is an inorganic acid less strong than the first, having a dissociation constant of less than about $10^{-1}$. A second acidic composition is formed by mixing from about 0.5% to about 20%, by weight, preferably from about 2% to about 15%, and more preferably from about 6% to 10%, of an organic hydroxy acid with water. The organic hydroxy acid has a greater chelating capability (generally at least twice) or iron binding efficiency as one or the other of the first and second inorganic acids. Acids with at least twice the ion binding efficiency of the inorganic acids include, for example, ascorbic acid, citric acid, lactic acid, malic acid and taltaric acid.

The two acidic compositions or solutions are then mixed to produce an acid core composition that inhibits microbial growth and is safe for use in food products. This composition preferably has a pH of less than one, yet will not adversely react with human tissue.

In a preferred embodiment, the first acid is hydrochloric acid, the second acid is phosphoric acid, and the organic hydroxy acid is citric acid. Generally, the quantities of the first acid will balance the quantity of the second acid such that less of the first acid will be required when using more of the second acid. A maximum quantity of the second acid is that amount which will require the addition of no first acid when admixed with the organic hydroxy acid to produce the low pH composition of the invention.

The acid composition of the present invention maintains the low pH and non-toxic qualities of conventional acidic compositions, yet, unlike these compositions, is safe to use in food and food-associated products, such as paper for packaging and wrapping food, food containers, food preserving agents and ingestible products.

In contrast, acids used in a number of conventional products, such as, for example, hydrofluoric, sulfuric, nitric, chloric, perchloric, chlorous, hydrofluoric, hydrosulfuric, fumaric, oxalic, phthalic, tartaric, acetic, acrylic, benzoic and carbonic acid, are not generally recognized as safe, and none are federally approved for use in ingestible products or products contacting ingestible products. Further, as many of the conventional acid-based solutions are toxic, disposal and handling of such compositions require special measures not necessary when utilizing compositions of the invention.

Another embodiment of the invention is directed to a pharmaceutical compound comprising a three acid composition, the three acid composition comprising: a first acid, wherein the first acid is an inorganic acid that dissociates nearly to completion in water; a second acid, wherein the second acid is an inorganic acid less strong than the first inorganic acid and has a dissociation constant of less than about $10^{-1}$; a third acid, wherein the third acid is an organic hydroxy acid which is weaker than the first and second acids, has a greater chelating capacity, generally at least twice, of either first or second acid, and has a dissociation constant of from about $10^{-1}$ to $10^{-5}$; and a pharmaceutical agent. Preferably, the three acids are GRAS acids.

Another embodiment of the invention is directed to a composition for processing food items comprising a three acid preservative consisting of: first inorganic GRAS acid that dissociates nearly to completion in water; a second inorganic GRAS acid less strong than the first acid and having a dissociation constant of less than about $10^{-1}$; and a third GRAS acid, the third GRAS acid being an organic hydroxy acid that has at least twice the chelating efficiency as either of the inorganic acids. Preferably, the organic hydroxy acid is weaker than the first and second acids and has a dissociation constant of from about $10^{-1}$ to $10^{-5}$. An especially preferred food processing composition comprises hydrochloric, phosphoric and citric acids.

Another embodiment of the invention is directed to a method of preserving food comprising the addition of a three acid preservative composition to a food substance.

The three acid preservative composition comprises: a first GRAS acid which is an inorganic acid that dissociates nearly to completion in water; a second GRAS acid, the second GRAS acid being an inorganic acid less strong than the first GRAS acid and having a dissociation constant of less than about $10^{-1}$; and a third GRAS acid, the third GRAS acid being an organic hydroxy acid weaker than the first and second GRAS acids, with chelating capability at least twice as great as either or both of the first and second GRAS acids and a dissociation constant from about $10^{-1}$ to $10^{-5}$.

Another embodiment of the invention is directed to a method for decontaminating surfaces comprising contacting the surface with an acid composition of the invention comprising: a first GRAS acid, wherein the first GRAS acid is an inorganic acid that dissociates nearly to completion in water; a second GRAS acid, wherein the second GRAS acid is an inorganic acid less strong than the first inorganic acid and has a dissociation constant of less than about $10^{-1}$; and a third GRAS acid, wherein the third GRAS acid is an organic hydroxy acid weaker than the first and second GRAS acids, but being at least twice as efficient as either or both of the first and second inorganic acids in its chelating ability and having a dissociation constant of from about $10^{-1}$ to $10^{-5}$.

Another embodiment of the invention is directed to a method for treating a surface to inhibit microbial growth on the surface comprising contacting the surface with a three acid composition according to the invention.

Other objects and advantages of the invention are set forth in part in the description which follows, and in part, will be obvious from this description, or may be learned from practice of the invention.

DESCRIPTION OF THE INVENTION

As embodied and broadly described herein, the present invention is directed to low pH acidic compositions that are generally recognized as safe. Compositions according to the invention are safe for use in food, beverage, or other ingestible products and do not irritate the skin. The present invention is useful in industrial, medical, military, and household applications. Medical applications include use on humans and animals. The invention also relates to formulations containing the acidic compositions of the invention, applications of these compositions, and to methods of making and using these compositions.

Many of the acidic compositions currently used in industrial, medical, military and household settings present health hazards to the user and are corrosive with prolonged exposure to the surfaces they contact. Use of these compositions often requires special protective clothing and application methods. Additionally, disposal of these toxic products in a manner which ensures the safety of the environment and personnel is costly and time consuming. Although some conventional compositions are less caustic to skin and, overall, less hazardous to the user than others, they are, nonetheless, not safe for use in food and beverages or in other ingestible products.

An acid composition that can be safely handled and applied directly to human skin has been discovered which, unlike conventional acid-based compositions, uses a minimum number of ingredients, all of which are federally approved for use in food and drink products and food- and drink-associated products. Compositions of the invention are also applicable for industrial, military and general household uses. In addition to being suitable for use on and by humans, the present invention is also appropriate for animals. The compositions of the invention are effective and may be used over a wide range of temperatures, including room temperature. Thus, the present invention provides an advantage over sterilants which require a power source or energy, such as beat (autoclaving). Moreover, acid compositions of the invention have a shelf life of one year or greater when stored at ambient temperature.

One embodiment of the invention is directed to a low pH acid composition comprised only of GRAS substances. GRAS substances are those substances which are approved for use in food, beverages and other ingestible products, and in products which contact these materials. Specifically, these substances, listed at 21 C.F. R. Part 182 and Part 184, are recognized by the FDA as safe for use in foods, beverages and ingestible products, and in products associated with foods and beverages. Such substances are generally considered non-carcinogenic. As such, the compositions of the invention are safe to use in association with food and drinks and other ingestible products.

In a preferred embodiment, three acids are used. The first acid is hydrochloric acid, the second acid is phosphoric acid, and the third acid is citric acid. In this embodiment, the first acid of the composition, hydrochloric acid, comprises between about zero to about 25 volume percent of the final composition, preferably between about 0.1 to 20 volume percent, and more preferably between about 5 to about 10 volume percent of the final composition. Hydrochloric acid is a strong inorganic acid which dissociates nearly to completion in water. Some particularity useful acid compositions of the invention contain about 0.1%, 0.2%, 0.5%, 1%, 2%, 3%, 4%, 5%, 6%, 8%, 10%, 12%, 14%, 15%, 18%, 20%, 21%, 22% and 24% of the first acid.

The second acid of the composition, phosphoric acid, is also an inorganic acid but is less strong than hydrochloric acid. Phosphoric acid thus functions as a conjugate base and accepts hydrogen ions (actually hydronium ions in aqueous solutions) from the stronger hydrochloric acid. The phosphoric acid comprises between about 0.1 to about 20 volume percent of the final composition and preferably between about 1 to 15 volume percent, and more preferably between about 5 to about 10 volume percent of the final composition. Some particularity useful acid compositions of the invention contain about 0.5%, 1%, 2%, 3%, 4%, 5%, 6%, 8%, 10%, 12%,13%, 14%, 15%,16% and 18% of the second acid.

The third acid is an organic acid (e.g. citric acid) belonging to the group of hydroxy carboxylic acids and is a weak acid relative to hydrochloric and phosphoric acids. Specifically, citric acid is a 6-carbon, tricarboxylic acid. Citric acid preferably comprises between about 1 to about 15 weight percent, preferably between about 5 to about 10 weight percent and more preferably between about 6 to about 9 weight percent of the final composition. Some particularity useful acid compositions of the invention contain about 0.5%, 1%,2%,3%,4%,5%,6%,8%, 10%, 12%, 13%, 14%, 15%, 16%, 17%, and 18%, by weight, of the organic hydroxy acid.

A preferred embodiment of the improved aqueous acidic composition of the invention may be prepared by a process involving the following steps:

(1) mixing at room temperature from about 5 to about 10 (most preferably 6.60) volume percent hydrochloric acid (HCl being principally responsible for the resulting pH) with from about 1 to about 5 (most preferably 4.49) volume percent phosphoric acid in a first container for a period of time sufficient to produce a homogenous mixture;

(2) mixing at room temperature in a second container from about 5 to about 10 (most preferably 7.50) weight percent citric acid with from about 85 to about 90 percent water for a period of time sufficient to result in thorough mixing; and (3) admixing at room temperature the hydrochloric/phosphoric acid mixture held in the first container into the citric acid/water mixture of the second container until a homogenous composition results.

The acid aqueous composition of the present invention is basically colorless (high concentrations of HCl produce a greenish to yellowish color), has a pH of less than one, will not harm human tissue, and contains only substances approved by the Food and Drug Administration to be GRAS substances. Thus, the resulting aqueous acidic composition is safe for use in food, drink, and other ingestible products. The composition of the present invention is also much less corrosive to metals than acid compositions at a similar pH. Delicate instruments such as, for example, dental instruments, surgical and other medical instruments, and computer parts, can be effectively cleaned using an acid composition of the invention without harming the delicate components or parts of the instrument or causing undue wear.

The acid composition of the present invention may be used alone or as the base, core or active component in the formulation of other solutions. Additional ingredients, if desired, may be added to the three acid composition depending on its intended purpose or application. Substances may be added to the core acid composition, for example, to increase the retention time of the product on the skin, to give an appealing color or scent to the composition, to produce a specific texture, or to increase the specificity of application of the composition. Additives such as anesthetic agents (e.g. lidocaine), pH indicator dyes and other dyes and contrast agents can be added depending on the application.

The compositions of the present invention are suitable for use in a plurality of food industry, household, military, medical and industrial settings. Just a few potential uses of the compositions of the present invention include: cleaning and disinfecting surfaces, instruments, foods and equipment; antimicrobial component for hygiene products, preparation of skin surface for injections, topical ointments, creams, gels, inhalants (generally used at concentrations of 5%, 4%, 3%, 2%, 1% or less), mouth and eye washes, activation of immune-response (e.g. stimulates non-specific immunity); anti-odorant; cleaning and disinfecting food items and food processing (e.g. removes coffee and tea stains), packaging and storage materials; pH- and/or microbial-control agent (swimming pools); a detoxifying/decontaminating composition for clean up of chemical spills or hazardous materials (HazMat) (decontamination showers) (eliminates toxic cloud/fumes from acid spills at various mixtures such as 10:90, 25:75, 60:40, 50:50, 40:60, 75:25 and 90:10 mix depending on the acid); manufacture of food processing, packaging and transportation items; detoxifying composition for industrial settings (i.e. paper mills and other industrial plants, and laboratories may use HCl and/or sulfuric acids; can treat HCl burns with invention); industrial showers (acid showers); manufacture of acid-containing solutions and products (i.e. batteries containing "battery acid" such as sulfuric acid; by mixing with invention, less toxic and less fuming); cleaning battery posts; sterilization or purification of water supply; non-toxic embalming agent; detoxification/deactivation of chemical and biological warfare agents; and cleaning air ducts.

Specific veterinary, dental and medical applications include wound cleaning and disinfecting, disinfecting and sterilizing floors, surfaces and instruments (dialysis apparatus), topical treatment of skin infection, treatment of topical irritants (poison ivy and poison oak), sterilization of indwelling devices (e.g. catheters, IV drips); anti-STD applications (i.e. suppositories, creams, gels, condoms, mouthwashes, douches); treatment of burns, sunburns, ear infections, insect bites, jellyfish stings, anti-coagulant, treatment of medical waste, and anti-fungal agents (e.g. anti-jock itch treatment, prevention or treatment of athlete's foot).

The invention can also be used as an anti-odorant to neutralize ammonia-based odors/wastes, biological specimens, chemical toilets, animal bedding and diapers. It may be used as an underarm deodorant. In connection with food, it may be used to spray produce, clean and disinfect food transport containers and fluid lines or any surface coming in contact with food and food serving materials. It may be applied to seafood as a deodorizer and be used to spray live animals or to spray meat before wrapping, etc. As an antibacterial, anti-fungal and sporicide, it may be used, for example, as an acidifier in home canning.

With respect to military applications, the invention may be used to decontaminate chemical warfare agents on personnel and surfaces, and given its broad spectrum of activity, is ideal for incorporation into bandages and sponges. The invention may be incorporated into a missile or other delivery device as a countermeasure to deactivate chemical warfare or biological agents (e.g. protein toxins such as anthrax, botulism and *E. coli*) delivered by or contained in another weapon system. It may be delivered to a broad contaminated area through the use of a fog/smoke generating device, crop-dusting or firefighting aircraft.

Applications also include use as a non-toxic embalming agent, anti-scale build-up and treatment of water supplies, electrolyte sports drink, treatment of personal items such as toothbrushes or hairbrushes, safety showers for certain industries using acids, acid spill or acid cloud clean up. It may be used as a silver or chrome polish, to remove oxidation build-up on heat exchangers, pipes and water heaters, to descale sinks, water storage tanks, showers and the like to remove barnacles, or to clean concrete. It may be used as a fixative for fabric dyes (pH indicator dyes bonded to cotton fabrics—dye retained after machine laundering; also may be used in wearable pH indicator garments which are acid or base sensitive). It may be used as a preservative for foods, biological specimens, forensic specimens and biological specimens and lumber. It may be used as a buffer for noxious solutions or to inhibit the corrosive properties of bleaching solutions. Further applications include etching aluminum or porcelain, and use as an anti-freeze or water purifier. Because the invention is compatible with pH indicator dyes, solution efficacy can be visually determined. Also, solutions have the potential for repeated re-use (i.e. can be recycled).

Another embodiment of the invention is directed to a pharmaceutical agent or compound containing the acid composition of the present invention. As will be clear to those of skill in the art, various substances may be added to the aqueous acidic composition of this invention as desired to produce a pharmaceutical agent. The terms "pharmaceutical agent" or "pharmaceutical compound" as used herein are used in their broadest possible sense and include, but are not limited to, medications and all types of therapeutic agents, whether taken orally, parenterally, topically, or by any other route. Useful substances which may be added to produce a pharmaceutical agent include, but are not limited to, anesthetic agents, alcohols, creams, gels, aloe vera, vitamin E, PFP (polyfluorenated perfluorate, e.g. TEFLON, FOMBLIN), moisturizers, emollients, surfactants, humectants, scents, colorants, glycerin, propylene glycol, emulsifiers, wetting agents, pH indicator dyes, medically-relevant dyes, contrasting agents, and carriers known in the art. Uses of the pharmaceutical agents or compounds formulated with the three acid composition include, but are not limited to, deodorants, mouthwashes, topical antimicrobial ointment for wounds, and compositions for the treatment of a wide variety of maladies, including dry skin, wrinkles, acne, age spots, sunburn, infections (viral, bacterial and fungal), insect bites and rashes. The pharmaceutical agent may be appropriate for use on mucous membranes, including the mouth and eyes. The pharmaceutical agent or compound can be brought into contact with the surface to be treated either directly or via applicators, including, but not limited to, sponges, towelettes and pads.

Another embodiment of the invention is directed to decontamination agents containing acid compositions of the invention. These agents are particularly useful in military and industrial applications. These decontamination agents provide protection from, or directly inactivate, a variety of toxic chemical agents, such as those used in chemical warfare, farming, and lawn care. Such toxic chemicals include, but are not limited to, insecticides, pesticides, mustards, nerve agents, blister agents, cholinesterases and cholinesterase inhibitors in general. Additionally, decontamination agents according to the invention are effective in the inactivation of biologically toxic molecules such as those used in warfare. Biologically toxic molecules include, but are not limited to, aflatoxins, biological toxins, exotoxins, endotoxins, poisons, phytotoxins, insect and animal venoms and mycotoxins. Because of the non-caustic nature of the acid compositions of the present invention, these decontamination agents may be applied either directly to the skin, or may be applied to clothing or other materials that come in contact with skin. Thus, the present invention is suitable for use by first-responders in decontaminating physical surfaces, treating wounds in humans or animals, and/or deactivating chemical agents including nerve agents.

In a preferred decontamination compound, a three acid composition is made into a reactive topical skin protectant which may be mixed with a perfluorinted polyether grease vehicle, a water-based vehicle, or other suitable vehicle. Use of alternative vehicles allows for flexibility in application of the topical protectant. The resulting decontamination/protection barrier is active over a broad temperature range of from about $-10°$ C. to about $50°$ C., and is stable for one year or longer when stored at ambient temperatures.

Another preferred embodiment is directed to a decontamination compound in which the acid composition is incorporated into towelettes or sponges. The use of these towelettes or sponges allows for safe and rapid detoxification of organophosphate compounds (e.g. nerve agents), as well as viruses, bacteria and toxic molecules. The towelettes or sponges are easily carried by personnel and used by first-responders in decontamination steps. The towelettes or sponges are active over a broad temperature range of from about $-10°$ C. to about $50°$ C., and have a shelf life of one year or longer.

Another embodiment of the invention is directed to cleansing agents containing the acid composition. These cleansing agents include, but are not limited to, glass cleansers, metal cleansers, household cleaning solutions (kitchen and bathroom), and solutions to remove oxidation build-up from pipes and water heaters and heat exchangers. In this use of the invention, detergents, soaps, scents or strong acids may be added as needed to the acid composition.

In a preferred cleansing agent, hydrochloric acid is added to the acid composition in ratios ranging from about 0.1 parts to 30 parts (by volume) of the acid composition to produce a solution suitable for use as a metal cleaner. Addition of more hydrochloric acid reduces the time required for cleaning; however, this may result in a product which irritates skin.

Another embodiment of the invention is directed to the use of the invention as an antimicrobial agent such as a disinfectant or sterilant. These disinfectants and sterilants may be used, for example, to sterilize drinking water, disinfect surfaces, treat wounds, sterilize hair care and manicure equipment, sterilize dental equipment, sterilize hospital clean rooms, sterilize tissue culture hoods in laboratories, and sterilize biological waste. The three acid composition of the present invention may also be used in cleaning or sterilizing containers used in the transportation and storage of food and drink, such as truck tanks, vats and fluid lines.

Substances including, but not limited to, perfumes, aerosols, dyes, alcohols, reducing agents, anesthetic agents, oxidizing agents, amines, amides, surfactants, creams, gels and other acids may be added to the compositions of the present invention as needed for a particular application.

Another embodiment of the invention is directed to a composition for processing food comprising a three acid preservative consisting of a first inorganic GRAS acid that dissociates nearly to completion in water, a second inorganic GRAS acid having a dissociation constant of less than about $10^{-1}$, and a third GRAS acid being an organic acid weaker than the first and second acids, and having a dissociation constant of from about $10^{-1}$ to $10^{-5}$. An especially preferred food processing composition comprises hydrochloric, phosphoric and citric acids.

Food processing compositions of the present invention may be suitable for decontaminating food items, such as, for example, meats, fruits or vegetables. In a preferred embodiment, the composition is applied to fruits and/or vegetables to remove or effectively destroy residual pesticides. The food processing composition may also be suitable for use as a de-odorize for seafood and as an antimicrobial treatment for meat products.

Another embodiment of the invention is directed to a method of preserving food comprising the addition of an acid preservative composition to a food substance, the acid preservative composition containing a first GRAS acid, the first acid being an inorganic acid that dissociates nearly to completion in water; a second GRAS acid, the second acid being an inorganic acid less strong than the first inorganic acid and having a dissociation constant of less than about $10^{-1}$; and a third GRAS acid, the third acid being an organic acid weaker than the first and second acids, the third acid having a dissociation constant of from about $10^{-1}$ to $10^{-5}$.

The above formulations and applications are intended to merely illustrate the wide range of utility of the compositions described herein and are not intended to be an exhaustive listing of all possible formulations and uses of compositions according to the invention. Also, as the list of substances approved by the U.S. Food and Drug Administration to be Generally Regarded As Safe (GRAS) is revised, so will be the acids available for use in the compositions of the invention. As will be clear to those of skill in the art, compositions that are safe for human ingestion or contact are likewise safe for ingestion or contact by other animals.

The following examples are offered to illustrate embodiments of the present invention, but should not be viewed as limiting the scope of the invention.

EXAMPLES

Example 1

Preparation of Aqueous Acid Composition

A typical antimicrobial solution can be prepared by first dissolving the solid citric acid in deionized water, admixing with phosphoric acid and then adding the required amount of 10N or 12N hydrochloric acid. The amount of the dissolved acids and deionized water may be precalculated to achieve the following range of concentration of the individual acids: citric, 6–10% (by weight), phosphoric acid, 5–10% (by volume), and hydrochloric acid, 0.1–5% (by volume).

An acid composition according to the invention was prepared using the following recipe.

Container #1: 170 ml of 75–80% concentrated phosphoric acid was added to 250 ml of 12N hydrochloric acid (which is approximately 28–32%). The mixture was thoroughly stirred. Ventilation was required as there were fumes from each acid and from the mixture.

Container #2: 0.6 lbs (9.6 oz.) of granular citric acid was thoroughly mixed in 0.8 gallons (102 oz.) of water until dissolved after which container #1 containing the phosphoric/hydrochloric acid mixture was added and thoroughly mixed. The resulting acid composition consisted of approximately one gallon. Fumes from the resulting mixture were substantially eliminated and the pH was approximately 0.07.

Example 2

Acid Composition as an Antimicrobial Solution

An *E. coli* C600 bacterial strain was obtained from a commercial source. This bacterium was grown at 37° C. overnight in 500 ml of Brain-Heart Infusion broth (Difco), previously sterilized in an autoclave (121° C., 15 psi, 15 minutes). After the bacterial culture reached mid log phase, organisms were centrifuged (~5,000 rpm) in 50 ml centrifuge tubes (Corning). The bacterial pellet was washed twice in 10 mM imidazole, 150 mM NaCl (pH 7.2), and once in distilled water before resuspending in distilled water to approximately $1.4 \times 10^9$ colony forming units per ml (cfu/ml).

Three sets of serial 10 fold dilutions ranging from undiluted to $10^{-9}$ of the acid composition generated in Example 1 were then made in sterile 1.5 ml eppendorf tubes using sterile distilled water. A specific volume (100 μl) of the previously made bacterial suspension was added to 100 μl of each dilution in each of the three sets of serial 10 fold acid composition dilutions.

The first set of bacteria and acid composition dilutions were incubated for 6 minutes at room temperature. The incubated cells were immediately centrifuged at 5,000 rpm for 30 seconds and the supernatant discarded. Each bacterial pellet from each dilution was resuspended in 200 μl of sterile distilled water and placed into separate plastic petri dishes. Sterile molten Brain-Heart Infusion (BHI) agar (~55° C.) was added to each petri dish containing the bacteria. Plates were allowed to solidify on the bench and were inverted and incubated at 37° C. until observable growth was evident. Bacterial colonies were conted and recorded as cfu/ml.

The same procedure was followed for the second and third sets of acid composition dilutions containing 100 μl aliquots of bacterial suspension. However, the second set was incubated for one hour and the third set was incubated for three hours. After washing, cells were washed with sterile distilled water, plated, and the plates incubated at 37° C. for 16–20 hours. The effectiveness of different dilutions of acid composition with relation to time, against the *E. coli* strain C600 is shown in Table 1.

TABLE 1

Effectiveness of Acid Composition as an Antimicrobial Agent on *E. coli* Strain C600

| Time (minutes) | Dilution | CFU on Plate | Log Reduction* |
|---|---|---|---|
| Bacterial Control | 100% Water | $5 \times 10^{10}$ cfu/ml | 0 |
| 6 | Undiluted | 0 | ~10 |
| 6 | $10^{-1}$ | >5000 (TNTC) | 0 |
| 6 | $10^{-2}$ | >5000 (TNTC) | 0 |
| 6 | $10^{-3}$ | >5000 (TNTC) | 0 |
| 60 | Undiluted | 0 | ~10 |
| 60 | $10^{-1}$ | 0 | ~10 |
| 60 | $10^{-2}$ | >5000 (TNTC) | 0 |
| 60 | $10^{-3}$ | >5000 (TNTC) | 0 |
| 180 | Undiluted | 0 | ~10 |
| 180 | $10^{-1}$ | 0 | ~10 |
| 180 | $10^{-2}$ | 42 | ~6.5 |
| 180 | $10^{-3}$ | >5000 (TNTC) | 0 |

*Initial bacterial population was $5 \times 10^{10}$ cfu/ml.

Effective dilutions of the acid composition were $10^{-1}$ and $10^{-2}$ for any of the three incubation times listed. All undiluted samples of the bacteriocidal agent were effective in reducing the *E. coli* bacterial culture by 10 logs. At $10^{-1}$ dilution, 6 minutes was insufficient time to effect the bacterial population of *E. coil*. At 60 and 180 minutes, the $10^{-1}$ dilution reduced the bacterial culture by 10 logs. At $10^{-2}$ dilution, 60 minutes was not effective in bacterial population reduction while 180 minutes was effective in reducing the bacterial count to $4.2 \times 10^3$ cfu/ml.

Example 3

Effectiveness of Acid Composition as an Antimicrobial Agent of *B. subtilis*

The bacterial strain used in this study was *Bacillus subtilis* strain #19659 obtained from the American Type Culture Collection (ATCC). This bacterium was grown at 28° C. overnight in 500 ml of sterilized complex medium (BHI broth; Difco). After the bacterial culture reached mid log phase, organisms were centrifuged (~5,000 rpm) in 50 ml centrifuge tubes (Corning). The bacterial pellet was washed two times in 10 mM imidazole (150 mM NaCl, pH 7.2) and once in distilled water before resuspending in distilled water to approximately $5 \times 10^{10}$ colony forming units per ml (cfu/ml).

Three sets of serial 10 fold dilutions ranging from undiluted to $10^{-9}$ of the acid composition of Example 1 were made in sterile 1.5 ml eppindorph tubes using sterile distilled water. A specific volume (100 µl) of the previously made bacterial suspension was added to each dilution in each of the three sets of serial 10 fold acid composition dilutions. The first set of bacteria with acid composition dilutions was incubated for 6 minutes at room temperature. Cells were immediately centrifuged at 5,000 rpm for 30 seconds and the supernatant was discarded. Each bacterial pellet from each dilution was resuspended in 200 µl of sterile distilled water and placed into separate plastic petri dishes. Sterile molten BHI agar (~55° C.) was added to each petri dish containing the bacteria and allowed to solidify. Solidified plates were inverted and incubated at 28° C. until observable growth was evident. Bacterial colonies were counted and recorded as cfu/ml.

The same procedure was followed for the second and third sets of acid composition dilutions containing 100 µl aliquots of bacterial suspension. However, the second set was incubated for one hour and the third set was incubated for three hours. After incubation, cells were washed with sterile distilled water, poured into plates and incubated at 28° C. for 16–20 hours. The effectiveness of different dilutions of acid composition with relation to time, against the *B. subtilis* (ATCC #19659) can be seen in Table 2.

TABLE 2

Effectiveness of Acid Composition as an Antimicrobial Agent of *B. subtilis* (ATCC #19659)

| Time (minutes) | Acid Composition Dilution | Cfu on Plate | Log Reduction* |
|---|---|---|---|
| Bacterial Control | 100% Water | $1.4 \times 10^9$ cfu/ml | 0 |
| 6 | Undiluted | 0 | ~9 |
| 6 | $10^{-1}$ | 0 | 0 |
| 6 | $10^{-2}$ | 0 | 0 |
| 6 | $10^{-3}$ | >5000 (TNTC) | 0 |
| 60 | Undiluted | 0 | ~9 |
| 60 | $10^{-1}$ | 0 | ~9 |
| 60 | $10^{-2}$ | 0 | 0 |
| 60 | $10^{-3}$ | >5000 (TNTC) | 0 |
| 180 | Undiluted | 0 | ~9 |
| 180 | $10^{-1}$ | 0 | ~9 |
| 180 | $10^{-2}$ | 0 | ~9 |
| 180 | $10^{-3}$ | >5000 (TNTC) | 0 |

*Initial bacterial population was $1.4 \times 10^9$ cfu/ml.

The effective dilutions of the acid composition against *B. subtilis* were $10^{-1}$ and $10^{-2}$ for all three of the incubation times listed. All undiluted samples of the bacteriocidal agent were effective in reducing the *B. subtilis* bacterial culture by approximately nine logs. At $10^{-3}$ dilution, none of the times tested were effective in reducing the bacterial population.

Example 4

Further Dilutions of Acid Composition

The bacterial strain used in this study was *Bacillus subtilis* strain #19659 from American Type Culture Collection (ATCC). This bacterium was grown at 28° C. overnight in 500 ml of sterilized complex medium (BHI broth from Difco). After the bacterial culture reached mid log phase, organisms were centrifuged (~5,000 rpm) in 50 ml centrifuge tubes (Corning). The bacterial pellet was washed two times in 10 mM imidazole (150 mM NaCl, pH 7.2) and once in distilled water before resuspending in distilled water to approximately $2.8 \times 10^9$ colony forming units per ml (cfu/ml).

One set of dilutions of the acid composition of Example 1 were then made which ranged from undiluted, $10^{-1}$, $10^{-2}$, and $10^{-3}$, as well as nine other dilutions between $10^{-2}$ and $10^{-3}$. All dilutions were made in sterile 1.5 ml eppendorf tubes using sterile distilled water. A specific volume (100 µl) of the previously made bacterial suspension was then added to each acid composition dilution. The bacteria and each dilution of acid composition were incubated for 60 minutes at room temperature. The cells were immediately centrifuged at 5,000 rpm for 30 seconds and the supernatant was discarded. Each bacterial pellet from each dilution was resuspended in 200 µl of sterile distilled water and placed into separate plastic petri dishes. Sterile molten BHI agar (~55° C.) was added to each petri dish containing the bacteria. Plates were allowed to solidify, inverted, and incubated at 28° C. until observable growth was evident.

Bacterial colonies were counted and recorded as cfu/ml. The effectiveness of different dilutions of acid composition with relation to time, against the B. subtilis (ATCC #19659) can be seen in Table 3.

TABLE 3

Effectiveness of Acid Composition as an Antimicrobial Agent on B. subtilis (ATCC #19659)

| Time (minutes) | Acid Composition Dilution | Cfu on Plate | Log Reduction* |
|---|---|---|---|
| Bacterial Control | 100% Water | $2.8 \times 10^9$ cfu/ml | 0 |
| 60 | Undiluted | 0 | ~9 |
| 60 | $10^{-1}$ | 0 | ~9 |
| 60 | $10^{-2}$ | 0 | ~9 |
| 60 | $10^{-2.1}$ | 0 | ~9 |
| 60 | $10^{-2.2}$ | 0 | ~9 |
| 60 | $10^{-2.3}$ | 0 | ~9 |
| 60 | $10^{-2.4}$ | 0 | ~9 |
| 60 | $10^{-2.5}$ | 0 | ~9 |
| 60 | $10^{-2.6}$ | 0 | ~9 |
| 60 | $10^{-2.7}$ | $2.1 \times 10^1$ | ~8 |
| 60 | $10^{-2.8}$ | $4.8 \times 10^4$ | ~6 |
| 60 | $10^{-2.9}$ | $6.3 \times 10^6$ | ~3 |
| 60 | $10^{-3}$ | >5000 (TNTC) | 0 |

*Initial bacterial population was $2.8 \times 10^9$ cfu/ml.

Effective dilutions of the acid composition against B. subtilis were from $10^{-1}$ to $10^{-2.6}$ for the 60 minute incubation time. Once again the undiluted sample of the bacteriocidal agent was effective in reducing the B. subtilis bacterial culture by approximately nine logs.

Example 5

Effectiveness of Acid Composition as an Antimicrobial Agent against E. coli

The acid composition of Example 1 was used for the following testing. Testing was performed using nalgene tubing (1/16 inch in diameter). A culture of Escherichia coli was passed through three 3-inch sections of tubing and allowed to incubate for 15 minutes at room temperature. One section of tubing was rinsed with one ml of sterile water and the portion of the water remaining in the tube was allowed to incubate for 15 minutes at room temperature. This was repeated using acid composition solution and a 10% solution for the remaining tubing sections. Each section was then rinsed with 0.5 ml of sterile water and the rinse was assayed for bacteria by plating.

TABLE 4

Effectiveness of Acid Composition as an Antimicrobial Agent against E. coli

| cfu/ml* (+/- SD) | Tubing Treatment |
|---|---|
| 455 +/- 120 | water |
| 2 +/- 2 | 10% Acid Composition |
| 0 | 100% Acid Composition |

*cfu/ml = colony-forming units per milliliter.

Example 6

Effectiveness of the Acid Composition as an Antimicrobial Agent against S. cerevisiae To determine the efficacy of the acid composition against fungal pathogens, the acid composition of Example 1 was used as an antifungal against Saccharomyces cerevisiae. Fungal cells were grown and mixed with either water or various concentrations of acid composition with water (50/50, vol./vol.). These were incubated for 15 minutes at room temperature followed by plating to determine viability. Percent survival, shown below, represents plate counts relative to the water control.

TABLE 5

Effectiveness of Acid Composition as an Antimicrobial Agent against S. cerevisiae

| % Survival (+/- SEM) | Acid Composition Concentration |
|---|---|
| 102 +/- 22 | 0% (100% water) |
| 6 +/- 4 | 10% Acid Composition |
| 0 | 100% Acid Composition |

Example 7

Preparation of a BC for Testing Efficacy as Decontamination Agent

A base compound (BC) according to the invention was prepared by mixing 200 ml hydrochloric acid (12N), 170 ml phosphoric acid and 125 grams citric acid generally as described in Example 1. BC was supplemented with additives and utilized in the reaction assays as described below. The test compounds produced were made by first forming BC, and then using BC for the direct addition of supplements. Unless otherwise stated, all additions, mixing, etc. were performed at room temperature. Liquids added as supplements at a given percent concentration refers to the volume to volume ratios of supplement to BC. For solids, the amount was weighed out, added to an aliquot of BC and allowed to dissolve, then added to the BC to achieve the appropriate final volume.

Example 8

Inhibition of CW-Mime Agents-Materials and Methods

Chemical Warfare (CW) agents and CW-like or mime agents include a number of classes of compounds utilizing different mechanisms of action. One such class, nerve agents, such as diisopropyl fluorophosphate (DFP), inhibits acetylcholinesterase. DFP also inhibits the activity of serine proteases like trypsin. Paraoxan, a DFP-like molecule, (diethyl p-nitrophenyl phosphate) has a chemistry similar to DFP. Like DFP, paraoxan inhibits trypsin. Because of the similarity, paraoxan was used, as described below, as a DFP mime or model to study the efficacy of BC and modified forms of BC to inactivate the enzyme-inhibiting ability of this agent. In the experiments which follow, trypsin coupled to agarose beads is used as an assay for paraoxan, using the standard calorimetric assay for trypsin, BAEE (N-benzoly-L-arginine ethyl ester). In addition to testing BC. reactive substances were also introduced into BC to test efficacy in inhibiting paraoxan.

By identifying agents that can prevent paraoxan from inactivating a serine protease, decontamination compounds can be identified and further developed. The relative safety of paraoxan, the ease of assay for a serine protease, and the large margin of safety of previously manufactured test compounds make paraoxan particularly useful for screening modified test compounds.

The ability of paraoxan to inhibit the serine protease trypsin was assessed by placing an aliquot of paraoxan into distilled water (at a ratio of 1:100, paraoxan:water), followed by mechanical mixing of the solution. This stock of paraoxan was then used for assays in which 10 µl of this paraoxan stock was mixed with 10 µl of one of the test compounds of the present invention (see below) and incubated for various time periods (5, 15, and 60 minutes). The reactions were stopped by the addition of 20 µl of 1 M imidazole, 100 mM NaCl, pH 7.8.

Paraoxan solutions were then incubated with the serine protease, trypsin, and the activity of the trypsin was monitored as described below. A trypsin stock solution was freshly prepared for each experiment by weighing out 10 mg, and resuspending this into 1 ml of ice cold distilled water until use (within 15–30 minutes). Trypsin activity was assessed by diluting the trypsin stock 100-fold in 10 mM imidazole, 100 mM NaCl, pH 7.8, and placing 50 µl of this solution into ELISA wells (three rows per individual test experiment). Paraoxan solutions prepared as described above were added to the trypsin. This was allowed to incubate for 30 minutes at room temperature. A 2-fold serial dilution of these mixtures were then performed using 10 mM imidazole, 100 mM NaCl, pH 7.8 for each incubation mixture of trypsin and paraoxan/test compound. A negative control was also prepared by omitting the addition of the paraoxan, and adding distilled water alone.

Azocoll (an azo-dye impregnated collagen) was used to detect serine protease activity and was the basis for screening the various test compounds. A sample of azocoll was diluted into 10 mM imidazole, 150 mM NaCl, pH 7.8 (10 mg/ml) and incubated at room temperature for 15 to 30 minutes before use. For distribution of the azocoll into ELISA plate test wells, 200 µl pipette tips were modified by cutting 2 to 3 mm off of the end of each tip which permitted the azocoll particles to be easily moved freely into and out of the pipettor. To insure that similar amounts of azocoll were distributed to each test well, the azocoll suspension was mixed prior to withdrawing the aliquots with the modified pipette tips, and the pipettor was flushed three times with the suspension, using the third uptake stroke to obtain the azocoll for each well. This volume (100 µll) was placed into each test well containing the serially-diluted trypsin and paraoxan/test compound mixtures prepared as described above.

Enzymatic activity was determined by visual inspection of the azocoll particles placed into the ELISA test wells after at least a 30 minute incubation period at room temperature. Maximal trypsin activity was determined by the examination of the negative controls, in which only trypsin and water were present. The development of soluble colored product indicated that protease activity had occurred and the maximal dilution of trypsin that could produce this color was taken as 100% trypsin activity. For each individual experiment, comparisons of activity were made relative to internal controls prepared for that experiment. Any diminution of the dilution of trypsin which could still produce a soluble, colored product would indicate that the trypsin activity had been inhibited. The level of maximum trypsin inhibition was taken as the paraoxan-water control described above. As was the case for the control for maximal trypsin activity, this control was performed for each individual trypsin stock solution preparation for each experiment performed. In addition, a control for each test compound alone, in the absence of paraoxan, was performed to insure that any inhibition of activity was due to the action of paraoxan, and not the test compound itself.

Results are expressed as integral numbers which represent the increase in the well number (or increase in dilution of trypsin) that protease activity could be detected. Results are given as whole integers, wherein the integer represents x in the expression $2^x$. An x value of 0 indicates no change, an x value of 1 indicates that the trypsin could be diluted by half and activity was detected, an x value of 2 indicates that the trypsin could be diluted by 4 and activity was visible, an x value of 3 diluted by 8, etc. The integer represents the mean of each set of results rounded to the nearest whole integer.

As described below, test compounds were added to solutions to determine if there was any effect on the extent of paraoxan-induced trypsin inhibition. These effects were detected by the development of soluble colored product from the azocoll at higher serial dilutions of the trypsin solutions relative to the paraoxan-water and trypsin incubation. For example, compositions of the present invention include derivatives of BC which contain oxime reagents. Another test compound contains amine. These derivative compositions based upon BC may be useful in optimizing a decontaminating compound for the destruction of CW agents and mimes. The results which follow indicate that BC, alone and in combination with other additives, does in fact effect the ability of paraoxan to inactivate trypsin.

Example 9

Effectiveness of Permanganate-Containing BC Solution in Deactivating Chemical Warfare Agents Permanganate-containing test compounds were produced by the addition of 0.1, 1 and 10 mM potassium permanganate to BC. These compounds were designated as TC02157-0.1, TC02157-1, and TC02157-10, respectively. Controls compounds or sham compounds consisting of these same permanganate concentrations in water were also assessed for activity and are designated as SC02157-0.1, -1, -10, respectively. After incubation with the paraoxan, each solution was supplemented with 1M imidazole, 100 mM NaCl (pH 7.8) to bring the pH to 7.8. The solutions were then added to the freshly prepared trypsin solutions and allowed to incubate. The trypsin solutions containing the paraoxan and test compound mixtures were then serially diluted, followed by the addition of the trypsin activity indicator, azocoll. After 30 to 60 minutes, the plate wells were inspected for trypsin activity, where a soluble colored product indicated that trypsin activity could be detected through the release of dye from the insoluble azocoll reagent. Each experiment represents the average, rounded to the nearest whole integer, of two sets of ELISA plates with 6 dilution series for each test compound and sham. The data in Table 6 represent the fold increase in trypsin activity due to the test compound over the trypsin activity treated with paraoxan alone/fold increase in trypsin activity due to the sham compound over the trypsin activity treated with paraoxan alone (test compound without permanganate was 1).

TABLE 6

Inhibition of the Paraoxan-Induced Inactivation of Trypsin by Test Compounds

| | TC02157-0.1/SC-0.1 | TC02157-1/SC-1 | TC02157-10/SC-10 |
|---|---|---|---|
| Expt 1 | 2/0 | 2/0 | 5/1 |
| Expt 2 | 1/0 | 2/0 | 4/1 |
| Expt 3 | 1/0 | 1/0 | 3/1 |

Indications from the above experiments (results presented as the mean increase for six separate experiments) suggested that the compounds supplemented with permanganate may serve to increase the ability of test compounds to inactivate paraoxan, and might serve as the basis for future tests of the inactivation of DFP directly. The ability of the sham compound SC-10 to inhibit activity was not expected, however the combination of BC with the permanganate increased the ability of the mixture to inhibit paraoxan activity with over a two-fold increase.

It was subsequently determined that further increases in permanganate ions, to values of 50, 100, and 250 mM concentrations, did not increase the ability of the test compounds to inhibit paraoxan activity (Table 7). The data in Table 7 represents the fold increase in trypsin activity due to the test compound over the trypsin activity treated with paraoxan alone/fold increase in trypsin activity due to the sham compound over the trypsin activity treated with paraoxan alone.

TABLE 7

Effect of Increasing Permanganate on Test Compounds

| TC02157-50/SC-50 | TC02157-100/SC-100 | TC02157-200/SC-200 |
|---|---|---|
| 5/1 | 5/2 | 5/2 |

These results suggest that a range of no more than 10 mM permanganate is most useful. Studies on the effect of time and temperature on the activity of the test compounds supplemented with permanganate were also performed. Experiments were designed to perform the paraoxan test inactivation assays at 4° C. in the test compounds supplemented with permanganate. No significant differences were found in the ability to inactivate paraoxan activity at the lower temperatures (not shown).

A series of time course experiments were decided upon due to the change in color of test compound solutions over time. For this series of time course experiments, test compounds were prepared supplemented with potassium permanganate, and a sequence of experiments were performed over the time course of one month. At days 0, 1, 3, 7, 14, 21, and 28 paraoxan inactivation assays were run at room temperature. Test compound was stored in a polypropylene bottle at room temperature during this time period for use in the assays. For any given day, an aliquot of the stored test compound (supplemented with 10 mM permanganate as described) was removed, and two separate sets of test assays were performed on two trypsin test solutions performed in triplicate as described in methods. The ability of this stored test compound to inhibit paraoxan activity is presented below, presented as the mean of the activity.

TABLE 8

Time Course of Activity of Permanganate-Supplemented Test Compounds

| | TC02157-0.1/SC-0.1 | TC02157-1/SC-1 | TC02157-10/SC-10 |
|---|---|---|---|
| Day 0 | 3/0 | 3/0 | 6/1 |
| Day 3 | 3/0 | 2/0 | 4/1 |
| Day 7 | 2/0 | 2/0 | 3/0 |
| Day 14 | 1/0 | 1/0 | 1/0 |
| Day 21 | 1/0 | 0/0 | −1/0 |
| Day 28 | 1/0 | 0/0 | −1/−1 |

The data shown in Table 8 represent the fold increase in trypsin activity over the trypsin inhibition by paraoxan alone on a given day, as described in methods. The decrease in the paraoxan-inhibiting activity of the test compound seen in these experiments indicate that permanganate ions may degrade the ability of the test compound to inhibit paraoxan activity. Similar experiments were performed using test compounds stored at 4° C. and at −20° C. in an attempt to delay or inhibit the reaction. No significant differences were seen in these experiments (not shown). Permanganate may be detrimental to the test compound activity under these conditions. Compounds based on supplements with permanganate may require a two-step procedure with a rapid mix prior to use.

Example 10

Efficacy of BC Mixed with Other Agents

The above results show that the test compounds supplemented with permanganate may serve as the basis for inactivation of DFP directly, however, the functional lifetime of the effectiveness of the compounds may have been compromised, as after 7 days a significant decrease in effectiveness was noted. The following experiments were performed in which BC was supplemented with other agents that have previously been implicated in extending the shelf-life of test compounds (not shown). Specifically, $ZnCl_2$ (10 μM), $MnCl_2$ (10 μM), and diethanolamine (5 μM, 50 μM, and 100 μM) were utilized as additives to the test compound TC02157-0.1 and the sham SC-0.1. These additions to the test compound were performed, and the resultant solutions were assayed for longevity as performed above. For the following results, the data are presented in terms of the relative difference (if positive) between the highest dilution of trypsin activity detected for the test compound minus that found for the sham compound. All ions were used at a concentration of 10 mM added in the chloride form. Diethanolamine concentrations of 5, 50, and 500 μM are presented as D5, D50, and D100, respectively, in Table 9 below.

TABLE 9

Effect of Zn, Mn, and Diethanolamine on the Loss of Activity of Permanganate-Supplemented Test Compounds

| TC02157-0.1 | +Zn | +Mn | +D5 | +D50 | +D100 |
|---|---|---|---|---|---|
| Day 0 | 3 | 3 | 3 | 3 | 3 |
| Day 3 | 3 | 2 | 3 | 3 | 3 |
| Day 7 | 3 | 2 | 2 | 2 | 2 |
| Day 14 | 2 | 1 | 1 | 1 | 2 |
| Day 21 | 1 | 1 | 1 | 1 | 2 |
| Day 28 | 1 | 0 | 1 | 1 | 1 |

The data shown in Table 9 represent the fold increase in trypsin activity over the trypsin inhibition by paraoxan alone on a given day, as described above. The results showed that both the $ZnCl_2$ and $MnCl_2$ did not significantly alter the loss of activity after 7 days, however, there was a slight increase in overall activity, possibly due to the divalent cations and/or their interaction with the permanganate. No difference was seen using any of the diethanolamine supplements described above. Similar results were seen when the experiment was repeated after a 14 day incubation. There was a noticeable color change in the solutions supplemented with diethanolamine after this period of time and a loss of activity. Incubation times of over 21 days, however, indicated that the inhibition of activity might be delayed by diethanolamine or Zn ions in combination with the permanganate-supplemented compound.

These studies indicate that the increase in activity attributed to the permanganate might result in a decrease in efficacy of compounds according to the invention within a short period of time. Concurrent work with other test compounds containing permanganate relative to control test compounds without permanganate had higher paraoxan inhibiting activities and did not lose this activity over similar time periods. In view of this, other supplements to BC were examined. Other supplements that were found to either show no enhancement of paraoxan-inhibiting ability or an incompatibility with the test assay system include mercaptoethanol, iodoacetamide, iodoacetic acid and thiosulfate ions.

Further experiments were carried out to test a BC composition containing 1% teri-butanol, 1% hydrogen peroxide, 100 µM $ZnCl_2$ and 10 mM hydroxylamine. This compound reverses the inhibitory effects of paraoxan on trypsin activity. BC composed of hydrochloric acid, phosphoric acid and citrate (as described in Example 1) was prepared and supplemented with various concentrations of zinc ions in the form of zinc chloride (0.1, 1, 10, 100 and 200 mM).

TABLE 10

Inhibition of Paraoxan-Induced Inactivation of Trypsin by Zn-supplemented BCs As a Function of Time after Production of Test Compounds

| Zinc Supplement (mM) | 0.1 | 1 | 10 | 100 | 200 |
|---|---|---|---|---|---|
| Activity, Day 0 | 2 | 2 | 3 | 1 | 0 |
| Activity, Day 7 | 2 | 2 | 3 | 1 | 0 |
| Activity, Day 21 | 2 | 2 | 4 | 1 | 0 |
| Activity, Day 28 | 2 | 2 | 3 | 1 | 0 |

Based on this study, it was determined that at very high concentrations of zinc, some direct inhibition of trypsin activity was occurring in this assay system during exposure of the trypsin to the test compound itself, as the controls containing no paraoxan were similarly inhibited, resulting in no differences being detected. The activity of the supplement at 10 mM, however, indicates that some augmentation can be detected. No decrease in activity was seen over the course of 28 days. Further experiments indicate that no significant change in activity occurred over a period of three months (not shown).

Other cations, such as Ca++, Cu++, Fe+++, Mn++, and Co++ were assessed for their ability to augment the paraoxan-inhibiting activity of the BCs. For the ions Ca and Mn, the assay system controls were altered such that these supplements could not be easily assessed due to some direct inhibition of the trypsin in the absence of paraoxan. Limited augmentation of activity was detected using Fe, Cu and Co; however, the slim increase declined rapidly upon storage.

BC was prepared and a series of test compounds containing various amounts of butanol (0.1, 0.5, 1, 5, 10, 20, and 30%). These butanol-supplemented compounds were then used in paraoxan inhibition assays as described previously. For the following results, the integers expressed are the changes in trypsin dilution with delectable protease activity relative to the unsupplemented BC alone. For these results, each positive integer represents a "1" will increase in trypsin activity (i.e. a two-fold increase). Any diminution in the dilution is represented by a similar, negative integer. A “0” indicates no change relative to the unsupplemented compound. Any positive integer would indicate that the ability of paraoxan to inhibit protease activity has been limited by the addition of the supplement. No detectable inhibition of trypsin activity was detected induced by the butanol in the absence of paraoxan (not shown).

TABLE 11

Effect of Butanol on the Inactivation of Paraoxan-Mediated Effects by Test Compounds

| Butanol % | 0.1 | 0.5 | 1 | 5 | 10 | 20 | 33 |
|---|---|---|---|---|---|---|---|
| Activity | 0 | 0 | 0 | 1 | 2 | 4 | 5 |

The ability of butanol to enhance the paraoxan-inhibiting activity of the BC at 20 to 33% concentration was seen over a period of one month (not shown). A shorter chain alcohol, propanol, was then tested in a similar set of experiments. An increase in activity (2-fold) was seen at the 33% concentration, with negligible enhancement of BC activity.

No change was noted with time for propanol. No activity enhancement was seen using the shorter chain alcohols ethanol and methanol (not shown). It should be noted that for butanol, the mixture can separate upon storage. The test compounds supplemented with butanol were premixed by shaking prior to distribution for testing.

Hydrogen peroxide supplemented BCs were prepared at peroxide concentrations of 0.1, 0.5, 1, 2, and 5% As presented for the butanol data above, the integers represent the increase in dilution which permitted detection of protease activity.

TABLE 12

Effect of Hydrogen Peroxide Addition on the Ability of Test Compounds to Deactivate Paraoxan-Mediated Trypsin Inhibition.

| Hydrogen Peroxide (%) | 0.1 | 0.5 | 1 | 2 | 5 |
|---|---|---|---|---|---|
| Activity | 0 | 0 | 1 | 1 | 1 |

A kinetic study on the lifetime of any enhancement detected was performed for hydrogen peroxide-supplemented compounds. It was noticed that after 1 day (and later determined that within 2 to 4 hours), no delectable change was seen in that no enhancement occurred after 2 to 4 hours of incubation prior to performing the assay.

Hydroxylamine hydrochloride was used as a supplement to the BC in concentrations of 1, 2, 5, 10, and 20% (wt./vol.). The effect of hydroxylamine is expressed as the change seen relative to BC not containing any supplement.

TABLE 13

Inactivation of Paraoxan-Mediated Inhibition of Trypsin by Hydroxylamine Supplemented BCs

| Hydroxylamine (%) | 1 | 2 | 5 | 10 | 20 |
|---|---|---|---|---|---|
| Activity, Day 0 | 0 | 0 | 1 | 2 | 1 |
| Activity, Day 45 | 0 | 0 | 2 | 1 | 1 |

No significant change in this activity has been detected for compounds stored at room temperature for up to 60 days (not shown). The oximes 2,3 butanedione monoxime (BDM) and 2-pyridine aldoxime methchloride (PAM) were also tested as supplements to BC. No inhibition of trypsin activity was seen caused by either of these oxime supplements alone in the absence of paraoxan. For these investigations, the integers represent the differences in dilutions of trypsin that showed protease activity, where positive integers are equivalent to an increase in the dilution of trypsin that still permits the detection of protease activity relative to unsupplemented BC. As in the immediately preceding cases, any positive activity integer would indicate that the ability of paraoxan to inhibit protease activity has been dampened by the addition of the supplement. BC supplemented with oxime reagents were tested at concentrations of 0.01%, 0.1%, 0.3%, 0.5%, 1%, 2%, and 5% (weight to volume).

TABLE 14

Effect of Oxime (PAM and BAM) Supplements on the Ability of Test Compounds to Inactivate Paraoxan-Mediated Reactions

| PAM (%)  | 0.01 | 0.1 | 0.3 | 0.5 | 1 | 2 | 5 |
|---|---|---|---|---|---|---|---|
| Activity | 0    | 0   | 0   | 1   | 2 | 2 | 2 |
| BDM (%)  | 0.01 | 0.1 | 0.3 | 0.5 | 1 | 2 | 5 |
| Activity | 0    | 0   | 0   | 0   | 1 | 1 | 0 |

In the case of PAM, the ability to inhibit Paraoxan was optimal at a 1% concentration. Similar results were obtained for BDM, however the PAM was more effective at all concentrations tested relative to BDM. The 1% concentrations of both reagents in BC were then supplemented with zinc chloride. No significant enhancement was noted except for the use of 10 mM zinc chloride in conjunction with PAM (not shown). Some increase in activity could be detected by the addition of the above supplements with PAM showing the most increase.

A new series of compounds were prepared that combined some of the supplements tested above in BC, using combinations of the supplements shown to be most effective in enhancing the "decon" activity of the test compounds in inhibiting the paraoxan-induced inhibition of trypsin. As a first step, zinc ions at 10 mM concentration were added to test compounds prepared supplemented with hydroxylamine at a 10% concentration. Results in the table below represent the difference in activity of this double-supplemented BC relative to the BC containing hydroxylamine alone. A similar set of experiments was performed using zinc (10 mM) added to butanol-supplemented (30%) BC. A time course of assessment of activity was performed for the solutions stored at room temperature. The data indicate that zinc may enhance the activity of the hydroxylamine while either not affecting or even limiting the butanol-supplemented BC. No significant differences in this were seen over the time course of one month.

TABLE 15

Effect of Zn (10 mM) Addition on the Ability Supplemented Test Compounds to Inhibit Paraoxan-Mediated Effects

|                  | Zn + Hydroxylamine | Zn + Butanol |
|---|---|---|
| Activity, Day 0  | 1 | 0  |
| Activity, Day 1  | 1 | -1 |
| Activity, Day 7  | 0 | 0  |
| Activity, Day 14 | 1 | 0  |
| Activity, Day 21 | 1 | -1 |
| Activity, Day 28 | 0 | 0  |

As can be seen in the foregoing example, butanol, hydroxylamine, zinc chloride and the oxime 2-pyridine aldoxime methchloride can enhance inactivation of the ability of compositions according to the invention to deactivate potentially toxic molecules. The effect of these supplements does not decay over time.

Example 11

Use of BC to Inactivate Other Agents

Solutions according to the invention have been used to kill virus and bacteria. BC at 20, 10 and 5% diluted with distilled water reduced type 1 polio virus concentration by at least $10^5$. Bacterial assays were also positive. A 15% strength solution of BC in water for 10 minutes resulted in less than 1% survival for *E. Coli* LP 1395 cells. For *Enterobacter aerogenes*, the survival was less than 0.5% under similar conditions. A 1% solution of BC inactivates botulinum toxin more than 99.99% within 1 minute.

Other embodiments and uses of the invention will be apparent to those skilled in the art from consideration of the specification and practice of the invention disclosed herein. All references cited herein, for whatever reason, are specifically incorporated herein by reference including U.S. patent application, entitled "Hypertonic Aqueous Solutions of Polybasic Acid Salts" filed contemporaneously herewith. The specification and examples should be considered exemplary only with the true scope and spirit of the invention indicated by the following claims.

What is claimed is:

1. An acidic solution for inhibiting microbial growth consisting essentially of an aqueous acidic core composition, said acidic solution comprising from about 50 to about 100 percent of said acidic core composition, said acidic core composition consisting of three acids that are ingestible and thereby safe for use in food and drink products and food- and drink-associated products, said acid core composition prepared by the steps of:

admixing from about 1 to about 5 volume percent of a first acid, said first acid being an inorganic acid that dissociates nearly to completion in water, with about 5 to about 10 volume percent of a second acid, said second acid being an inorganic acid less strong than said first inorganic acid, said second acid having a dissociation constant of less than about $10^{-1}$, to produce a first acidic composition; and admixing from 6 to about 10 weight percent of a hydroxy acid, having at least twice the chelating capability of said first and second acids, with water to produce a second acidic composition; and admixing said first acidic composition with said second acidic composition to produce said acid core composition having a pH of less than one and wherein said acidic core composition will not react with human tissue.

2. The acidic solution of claim 1 wherein the first acid is hydrochloric acid.

3. The acidic solution of claim 1 wherein the second acid is phosphoric acid.

4. The acidic solution of claim 1 wherein the hydroxy acid is an organic acid.

5. The acidic solution of claim 1 wherein the hydroxy acid is a weak acid relative to said first and second acids, said hydroxy acid having a dissociation constant of from about $10^{-1}$ to $10^{-5}$.

6. The acidic solution of claim 1 wherein the hydroxy acid serves as a conjugate base to said first inorganic acid.

7. The acidic solution of claim 1 wherein the first acid of said acidic core composition is safe for use in food and drink products and in food- and drink-associated products.

8. The acidic solution of claim 1 wherein the second acid of said acidic core composition is safe for use in food and drink products and in food- and drink-associated products.

9. The acidic solution of claim 1 wherein the hydroxy acid is a hydroxy carboxylic acid.

10. The acidic solution of claim 9 wherein the hydroxy carboxylic acid is selected from the group consisting of ascorbic, citric, lactic, malic and tartaric acids.

11. The acidic solution of claim 1 wherein the hydroxy acid is a tricarboxylic acid.

12. The acidic solution of claim 1 wherein the hydroxy acid consists of at least three carbon atoms.

13. The acidic solution of claim 1 wherein the hydroxy acid is an acid safe for use in food and drink products and in food- and drink-associated products.

14. The acidic solution of claim 1 wherein the hydroxy acid is citric acid.

15. The acidic solution of claim 1 wherein the solution is safe for use in ingestible products.

16. The acidic solution of claim 1 wherein the solution is safe for use on surfaces that contact ingestible products.

17. The acidic solution of claim 1 wherein the pH of said solution is less than one.

18. The acidic solution of claim 1 wherein the solution is nonreactive with human skin.

19. The acidic solution of claim 1 wherein the acidic core composition is substantially non-corrosive to metals.

20. The acidic solution of claim 1 wherein the solution is substantially non-corrosive to metals.

21. A composition for processing food comprising an aqueous acidic core composition consisting essentially of:

about 0.1 to about 25 volume percent of a first GRAS acid, said first GRAS acid being an inorganic acid that dissociates nearly to completion in water;

about 0.5 to about 25 volume percent of a second GRAS acid, said second GRAS acid being an inorganic acid less strong than said first GRAS acid and having a dissociation constant of less than about $10^{-1}$; and 6 to about 20 weight percent of a third GRAS acid, said third GRAS acid being an organic hydroxy acid weaker than said first and second GRAS acids, said third GRAS acid having a dissociation constant of from about $10^{-1}$ to $10^{-5}$, and having chelating capability of at least twice said first and second GRAS acids.

22. The composition of claim 21 wherein the first GRAS acid is hydrochloric acid, the second GRAS acid is phosphoric acid and the third GRAS acid is citric acid.

23. A method of presenting food comprising the step of adding a three acid preservative composition to a food substance, said three acid preservative composition consisting essentially of:

about 0.1 to about 25 volume percent of a first GRAS acid, said first GRAS acid being an inorganic acid that dissociates nearly to completion in water;

about 0.5 to about 25 volume percent of a second GRAS acid, said second GRAS acid being an inorganic acid less strong than said first GRAS inorganic acid and having a dissociation constant of less than about $10^{-1}$; and 6 to about 20 weight percent of a third GRAS acid, said third GRAS acid being an organic acid weaker than said first and second GRAS acids, said third GRAS acid having a dissociation constant of from about $10^{-1}$ to $10^{-5}$, and having chelating capability of at least twice said first and second GRAS acids.

24. The method of claim 23 wherein the first GRAS acid is hydrochloric acid, the second GRAS acid is phosphoric acid and the third GRAS acid is citric acid.

* * * * *

UNITED STATES PATENT AND TRADEMARK OFFICE
CERTIFICATE OF CORRECTION

PATENT NO. : 6,375,976 B1
APPLICATION NO. : 09/487174
DATED : April 23, 2002
INVENTOR(S) : Roden et al.

It is certified that error appears in the above-identified patent and that said Letters Patent is hereby corrected as shown below:

In the Specification

| | |
|---|---|
| Column 2, line 59 | Delete "prferably", Insert --preferably-- |
| Column 3, line 7 | Delete "taltaric", Insert --tartaric-- |
| Column 3, line 9 | Delete "acid", Insert --acidic-- |
| Column 4, line 6 | Delete "$10^{1}$", Insert --$10^{-1}$-- |
| Column 4, line 18 | Delete "$10^{1}$", Insert --$10^{-1}$-- |
| Column 5, line 5 | Delete "beat", Insert --heat-- |
| Column 5, line 29 | Delete "particularity", Insert --particularly-- |
| Column 5, line 42 | Delete "particularity", Insert --particularly-- |
| Column 5, line 53 | Delete "particularity", Insert --particularly-- |
| Column 9, line 41 | Delete "de-odorize", Insert --deodorizer-- |
| Column 10, line 63 | Delete "conted", Insert --counted-- |
| Column 11, line 31 | Delete "*coil*", Insert --*coli*-- |
| Column 11, line 54 | Delete "eppindorph", Insert --Eppendorf-- |

UNITED STATES PATENT AND TRADEMARK OFFICE
CERTIFICATE OF CORRECTION

PATENT NO. : 6,375,976 B1
APPLICATION NO. : 09/487174
DATED : April 23, 2002
INVENTOR(S) : Roden et al.

It is certified that error appears in the above-identified patent and that said Letters Patent is hereby corrected as shown below:

| | |
|---|---|
| Column 14, line 56 | Delete "BC.", Insert --BC,-- |
| Column 15, line 40 | Delete "100µll", Insert --100µl-- |
| Column 16, line 31 | Delete "Controls", Insert --Control-- |
| Column 19, line 13 | Delete "teri-butanol", Insert --tert-butanol-- |
| Column 19, line 32 | Delete "itwas", Insert --it was-- |
| Column 19, line 57 | Delete "delectable", Insert --detectable-- |
| Column 19, line 59 | Delete "a "1" will", Insert --an-- |
| Column 19, line 60 | Delete "i.e. a two-fold increase", Insert --i.e., a "1" represents a two-fold increase-- |
| Column 20, line 23 | Delete "5%", Insert --5%.-- |

In the Claims

| | |
|---|---|
| Column 22, line 25, Claim 1 | Delete "acid", Insert --acidic-- |
| Column 22, line 40, Claim 1 | Delete "acid", Insert --acidic-- |

UNITED STATES PATENT AND TRADEMARK OFFICE
CERTIFICATE OF CORRECTION

PATENT NO. : 6,375,976 B1
APPLICATION NO. : 09/487174
DATED : April 23, 2002
INVENTOR(S) : Roden et al.

It is certified that error appears in the above-identified patent and that said Letters Patent is hereby corrected as shown below:

Column 24, line 8, Claim 23    Delete "presenting",
Insert --preserving--

Signed and Sealed this

First Day of May, 2007

JON W. DUDAS
*Director of the United States Patent and Trademark Office*

(12) EX PARTE REEXAMINATION CERTIFICATE (5257th)
United States Patent
Roden et al.

(10) Number: US 6,375,976 C1
(45) Certificate Issued: Jan. 17, 2006

(54) MULTI-PURPOSE ACID COMPOSITIONS

(75) Inventors: Ernest G. Roden, Hodge, LA (US); John R. Dankert, Lafayette, LA (US)

(73) Assignee: SteriFx TM, Inc., Shreveport, LA (US)

Reexamination Request:
No. 90/007,246, Oct. 5, 2004

Reexamination Certificate for:
Patent No.: 6,375,976
Issued: Apr. 23, 2002
Appl. No.: 09/487,174
Filed: Jan. 19, 2000

Related U.S. Application Data

(60) Provisional application No. 60/116,628, filed on Jan. 19, 1999.

(51) Int. Cl.
*A61K 47/00* (2006.01)
*A61K 7/00* (2006.01)

(52) U.S. Cl. .................. 424/439; 424/65; 424/401; 424/404; 424/436

(58) Field of Classification Search ................. 424/439, 424/65, 401, 404, 436
See application file for complete search history.

(56) References Cited

U.S. PATENT DOCUMENTS

| | | | |
|---|---|---|---|
| 4,084,747 A | 4/1978 | Alliger | 239/4 |
| 4,483,887 A | 11/1984 | Garcia | 427/436 |
| 4,647,458 A | 3/1987 | Ueno et al. | 424/128 |
| 4,970,014 A | 11/1990 | Garcia | 252/79.3 |

FOREIGN PATENT DOCUMENTS

| | | |
|---|---|---|
| EP | 0148709 | 7/1985 |
| GB | 842034 | 7/1961 |
| GB | 880521 | 10/1961 |
| JP | 7165510 | 6/1995 |
| JP | 870721 | 3/1996 |
| WO | WO 9740670 | 11/1997 |

OTHER PUBLICATIONS

European Search Report (EP 03 07 5875), Jul. 23, 2003.
PCT International Search Report (PCT/US00/01107), Sep. 6, 2000.
Restaino, L, et al., "Effects of Acids on Potassium Sorbate Inhabitation of Food Related Microorganisms in Culture Media", *J Food Sci* 1982; 47(1):134–138, 143.
Reid, James D., "The Disinfectant Action of Certain Organic Acids", *Am. J. Hygiene,* Jan. 22, 1932, pp. 540–556.
Poli, G, et al., "Virucidal Activity of Organic Acids", *Food Chem.,* vol. 4, No. 4, pp. 251–258.
Doores, S., "Antimicrobials in Food", Organic Acids in A.L. Branen and M.P. Davidson, 1983, pp. 75–108.

*Primary Examiner*—Jyothsna Venkat

(57) ABSTRACT

The invention relates to solutions containing acidic compositions that have a pH of less than 1, are non-caustic to human tissue and are safe for human ingestion. These compositions may be used as the sole or major component of solutions such as cleansers, pharmaceuticals, food preservatives and disinfectants. The acidic compositions may be used in medical, industrial, military and household applications. The invention also relates methods of administering and using the acidic compositions of the invention.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–24 is confirmed.

* * * * *